United States Patent
Saha et al.

(10) Patent No.: US 12,146,931 B2
(45) Date of Patent: Nov. 19, 2024

(54) IDENTIFICATION OF ADVISORY REGIONS IN BREAST MAGNETIC RESONANCE IMAGING

(71) Applicant: KONINKLIJKE PHILIPS N.V., Eindhoven (NL)

(72) Inventors: Indrajit Saha, Gurgaon (IN); Ulrich Wolfgang Katscher, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 130 days.

(21) Appl. No.: 17/913,293

(22) PCT Filed: Mar. 17, 2021

(86) PCT No.: PCT/EP2021/056746
§ 371 (c)(1),
(2) Date: Sep. 21, 2022

(87) PCT Pub. No.: WO2021/191007
PCT Pub. Date: Sep. 30, 2021

(65) Prior Publication Data
US 2023/0152404 A1 May 18, 2023

(30) Foreign Application Priority Data
Mar. 26, 2020 (EP) ..................... 20165864

(51) Int. Cl.
*G01R 33/56* (2006.01)
*A61B 5/00* (2006.01)
(Continued)

(52) U.S. Cl.
CPC .......... *G01R 33/5607* (2013.01); *A61B 5/055* (2013.01); *A61B 5/4312* (2013.01);
(Continued)

(58) Field of Classification Search
CPC ................ G01R 33/5607; G01R 33/50; G01R 33/56341; G01R 33/5608;
(Continued)

(56) References Cited

U.S. PATENT DOCUMENTS

| | | | | |
|---|---|---|---|---|
| 2009/0018432 A1* | 1/2009 | He | .................... | G01R 33/4808 600/409 |
| 2017/0018080 A1* | 1/2017 | Yokosawa | ............ | A61B 5/7435 |
| 2021/0161394 A1* | 6/2021 | Geethanath | ............ | G16H 50/20 |

FOREIGN PATENT DOCUMENTS

WO 2012070951 A1 3/2012

OTHER PUBLICATIONS

Shin J, Kim MJ, Lee J, Nam Y, Kim MO, Choi N, Kim S, Kim DH. Initial study on in vivo conductivity mapping of breast cancer using MRI. J Magn Reson Imaging. Aug. 2015;42(2):371-8. doi: 10.1002/jmri.24803. Epub Nov. 21, 2014. PMID: 25413153.

Mori N et al., "Diagnostic value of electric properties tomography (EPT) for differentiating benign from malignant breast lesions: comparison with standard dynamic contrast-enhanced MRI". Eur Radiol. 2019;29:1778-1786.

Hancu I et al., "Distortion correction in diffusion weighted imaging of the breast: performance assessment of prospective, retrospective and combined (prospective+ retrospective) approaches" Magn Reson Med. 2017; 78: 247-253.

(Continued)

*Primary Examiner* — Bo Joseph Peng

(57) ABSTRACT

Disclosed herein is a method of medical imaging. The method comprises: receiving (200) an echo planar diffusion weighted magnetic resonance image (122) of a region of interest (309) descriptive of breast tissue; receiving (202) a fat suppressed T2 weighted magnetic resonance image (124) descriptive of the region of interest; segmenting (204) the echo planar diffusion weighted magnetic resonance image to identify high diffusion rate regions (128); segmenting (206) the fat suppressed T2 weighted magnetic resonance image to identify tissue regions (130); identifying (208) a portion of the tissue regions as advisory regions (134) by inputting the high diffusion rate regions and the tissue regions into an image processing module; and providing (210) the advisory regions as a segmentation of the fat suppressed T2 weighted magnetic resonance image.

16 Claims, 4 Drawing Sheets

(51) Int. Cl.
  *A61B 5/055* (2006.01)
  *G01R 33/50* (2006.01)
  *G01R 33/563* (2006.01)
  *G06T 7/00* (2017.01)
  *G06T 7/11* (2017.01)
  *G06T 7/136* (2017.01)
  *G06T 7/174* (2017.01)

(52) U.S. Cl.
  CPC ....... *G01R 33/50* (2013.01); *G01R 33/56341* (2013.01); *G06T 7/0012* (2013.01); *G06T 7/11* (2017.01); *G06T 7/136* (2017.01); *G06T 7/174* (2017.01); *G06T 2207/10088* (2013.01); *G06T 2207/20084* (2013.01); *G06T 2207/30068* (2013.01)

(58) Field of Classification Search
  CPC . G01R 33/56554; A61B 5/055; A61B 5/4312; G06T 7/0012; G06T 7/11; G06T 7/136; G06T 7/174; G06T 2207/10088; G06T 2207/20084; G06T 2207/30068
  See application file for complete search history.

(56) References Cited

OTHER PUBLICATIONS

Dong et al: "Preoperative prediction of sentinel lymph node metastasis in breast cancer based on radiomics of T2-weighted fat-suppression and diffusion-weighted MRI II" European Radiology, Springer International, Berlin, DE, vol. 28, No. 2, Aug. 21, 2017 (Aug. 21, 2017), pp. 582-591.
Jose R. Teruel et al: "Inhomogeneous static magnetic field-induced distortion correction applied to diffusion weighted MRI of the breast at 3T", Magnetic Resonance in Medicine., vol. 74, No. 4, Oct. 16, 2014 (Oct. 16, 2014), pp. 1138-1144.
Murakami et al: "Correlation between 18F-FDG uptake on PET/MRI and the level of tumor-infiltrating lymphocytes (TILs) in triple-negative and HER2-positive breast cancer" European Journal of Radiology, Elsevier Science, NL, vol. 123, Dec. 23, 2019.
Shin Hee Jung et al: "Prediction of low-risk breast cancer using perfusion parameters and apparent diffusion coefficient" Magnetic Resonance Imaging, vol. 34, No. 2, Feb. 2016 (Feb. 2016), pp. 67-74.
International Search Report and Written Opinion from PCT/EP2021/056746 mailed Apr. 9, 2021.

\* cited by examiner

IDENTIFICATION OF ADVISORY REGIONS IN BREAST MAGNETIC RESONANCE IMAGING

CROSS REFERENCE TO RELATED APPLICATIONS

This application is a U.S. national phase application of International Application No. PCT/EP2021/056746 filed on Mar. 17, 2021, which claims the benefit of EP Application Ser. No. 20/165,864.8 filed on Mar. 26, 2020 and is incorporated herein by reference.

FIELD OF THE INVENTION

The invention relates to Magnetic Resonance Imaging, in particular to the screening of breasts using magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Various quantities or properties of the subject can be measured spatially using MRI.

International patent application WO2012070951A1 discloses a process for distinguishing ex vivo between benign and malign tumors in tissues such as soft tissues and particularly breast tissue through the registration and comparison of measurement data from dynamic contrast-enhanced magnetic resonance imaging (DCE-MRI) and dynamic susceptibility contrast-enhanced magnetic resonance (DSC) imaging of the tumors. The process is adjusted to initially performing two dynamic MRI pulse sequences in an interleaved mode during parenteral administration of an MR contrast substance, wherein one of said pulse sequences is optimized for high spatial resolution and the other pulse sequence is adjusted for high temporal resolution, the high-temporal dissolved sequence further comprising a double echo-collection being sensitive towards both DCE and DSC for generating a number of different biomarker data such as pharmacokinetic biomarker data, descriptive DCE biomarkers and descriptive DSC biomarkers, and subsequently normalizing and comparing said data with corresponding data from corresponding benign and malign tumors, respectively. From each tumor volume there is preferably collected biomarkers for the 95-percentile identifying most of the abnormal kinetic properties (belonging to the relevant biomarker).

SUMMARY OF THE INVENTION

The invention provides for a medical system, a computer program, and a method in the independent claims. Embodiments are given in the dependent claims.

The screening of breast tissue for abnormal tissues is typically performed using X-ray based mammography. Embodiments may provide an improved means of locating advisory regions in breast tissue using magnetic resonance images. To achieve this, two types of images are used. Echo planar diffusion weighted magnetic resonance images are used to locate high diffusion rate regions. The high diffusion rate regions may for example be a label for regions that have a diffusion rate above a predetermined diffusion rate threshold. This technique is very effective in identifying abnormal tissue regions. However, the echo planar diffusion weighted magnetic resonance images may contain spatial distortions. The abnormal tissue can be identified, but then its true location may be uncertain.

The high diffusion rate regions may, for example, alternatively be referred to as identified diffusion rate regions.

To provide the proper localization, a fat suppressed T2 weighted magnetic resonance image is used. The fat suppressed T2 weighted magnetic resonance image is segmented to identify tissue regions. Since fat or lipid suppression is used these segmentations may be considered to be fat-free tissue regions or adipose-free tissue regions. The resulting tissue regions then contain segmentations for normal tissue structures in the breast as well as any abnormal structures.

An imaging processing module is then used to identify a portion of the tissue regions as advisory regions. The imaging processing module may be configured to use spatial, volume, or shape-based relationships between the high diffusion rate regions and the tissue regions to identify the spatial location of the tissue regions that are responsible for causing the high diffusion rate regions.

In one aspect the invention provides for a medical system that comprises a memory storing machine-executable instructions. The medical system further comprises a computational system that is configured for controlling the medical system. The medical system may take different forms in different examples. In one example the medical system could be a workstation. In another example the medical system could be a remote server or the like which provides image processing and reconstruction services for magnetic resonance imaging. In another example the medical system is a system that includes a medical imaging system such as a magnetic resonance imaging system.

Execution of the machine-executable instructions causes the computational system to receive an echo planar diffusion-weighted magnetic resonance image of a region of interest descriptive of breast tissue.

Execution of the machine-executable instructions further causes the computational system to receive a fat-suppressed T2-weighted magnetic resonance image descriptive of the region of interest. There may be a registration between the echo planar diffusion-weighted magnetic resonance image and the fat-suppressed T2-weighted magnetic resonance image so that the regions of interest are identical or are equivalent. Execution of the machine-executable instructions further causes the computational system to segment the echo planar diffusion-weighted magnetic resonance image to identify high diffusion rate regions.

There may be different means of identifying the high diffusion rate regions, however one way would be to threshold the echo planar diffusion-weighted magnetic resonance image. The identification of high diffusion rate regions may identify tissue that has a pathology such as being a malignant tumor. The echo planar diffusion-weighted magnetic resonance images may be good at detecting such pathologies or tissue types, however, there is often distortion of the echo planar diffusion-weighted magnetic resonance images. It may therefore be possible to then identify such tissue types but the exact location may be uncertain.

Execution of the machine-executable instructions further causes the computational system to segment the fat-suppressed T2-weighted magnetic resonance images to identify tissue regions. These tissue regions may for example be non-fat or non-adipose tissue. Since the image is fat suppressed the tissue regions that are identified may exclude adipose or fat tissue. Execution of the machine-executable instructions further causes the computational system to identify a portion of the tissue regions as advisory regions by inputting the high diffusion rate regions and the tissue regions into an image processing module.

The use of the term advisory region indicates a region which may be provided or highlighted to a physician or other healthcare provider for further review or inspection. The image processing module may for example be used to correlate the tissue regions with the high diffusion rate regions. In the fat-suppressed T2-weighted magnetic resonance image there are many portions of tissue which may be identified. There may for example be glandular tissue in the breast as well as fibrous, supportive or connective tissue. There may also be additionally ligaments and scar tissue. This is in addition to any cancers or tumors that may also be present.

In a magnetic resonance image, it is often not practical to differentiate these tissue types. The echo planar diffusion-weighted magnetic resonance images on the other hand provide information about regions of the breast that have a high diffusion rate region. That is to say the diffusion rate regions have a diffusion above a predetermined threshold. Correlating the high diffusion rate regions with the tissue regions may enable the identification of the advisory regions and assist a physician. Execution of the machine-executable instructions further causes the computational system to provide the advisory regions as a segmentation of the fat-suppressed T2-weighted magnetic resonance image. The T2-weighted magnetic resonance image may therefore be displayed with the advisory regions marked or highlighted. This for example may aid a physician in planning further medical investigations or procedures.

It may be mentioned that the above may be performed in both two- and three-dimensional imaging. The fat-suppressed T2-weighted magnetic resonance image and the echo planar diffusion-weighted magnetic resonance image may be a two-dimensional image, a collection of two-dimensional slices or a full three-dimensional dataset.

In another embodiment the echo planar diffusion-weighted magnetic resonance image is a high b-value echo planar diffusion-weighted magnetic resonance image. The use of a high b-value echo planar diffusion-weighted magnetic resonance image may be beneficial because it may be useful in identifying high diffusion rate regions that could possibly contain tumorous or cancerous tissue. However, the use of the high b-value echo planar diffusion-weighted magnetic resonance image may cause larger distortions of the image. The identification of the advisory regions using the tissue regions from the fat-suppressed T2-weighted magnetic resonance image enables both the identification of the location as well as the high diffusion rate regions. The use of the label "high-b value" is a label which may be interpreted as indicating that the image was acquired using a b-value which may cause geometric distortions of the image.

In another embodiment execution of the machine-executable instructions further causes the computational system to receive a conductivity map descriptive of the region of interest. Execution of the machine-executable instructions further causes the computational system to calculate a conductivity measure of each of the advisory regions using the conductivity map. The conductivity measure may be a statistical value or measure which is calculated for the voxels which are identified as an advisory region. This may include various statistical quantities such as an average conductivity as well as minimum and maximum and mean values of the conductivity.

In another embodiment the advisory regions are used to define boundaries during calculation of the conductivity map.

Execution of the machine-executable instructions further causes the computational system to assign a classification of each of the advisory regions according to the conductivity measure. The conductivity measure may be very dependent upon various ion types such as sodium. If the advisory regions have both a high diffusion rate above a particular high diffusion rate value as well as an average conductivity or other conductivity measure above a predetermined threshold it may indicate that the particular advisory region is cancerous or should be investigated further by the physician.

In another embodiment execution of the machine-executable instructions further causes the computational system to render the advisory regions as an overlay on the fat-suppressed T2-weighted magnetic resonance image.

In another embodiment execution of the machine-executable instructions further causes the computational system to render the classification of each of the advisory regions according to or using the conductivity measure.

For example, advisory regions which have a conductivity measure above a predetermined conductively measure threshold could be highliged on a display or rendering. In another example a rendering could rank or assign an order in which the advisory regions are recommended to be investigated. A user interface could display the rank on the rendering or the user interface could have a control which an operator can sequentially highlight the advisory regions according to the rank.

In another embodiment the medical system further comprises a magnetic resonance imaging system configured to acquire k-space data from an imaging zone. The memory further contains first pulse sequence commands and second pulse sequence commands. The first pulse sequence commands are configured to acquire first k-space data according to an echo planar diffusion-weighted magnetic resonance imaging protocol. The second pulse sequence commands are configured to acquire second k-space data according to a T2-weighted magnetic resonance imaging protocol. The second pulse sequence commands are fat or lipid suppressing.

Execution of the machine-executable instructions further causes the computational system to acquire the first k-space data from a region of interest containing the breast tissue by controlling the magnetic resonance imaging system with the first pulse sequence commands. Execution of the machine-executable instructions further causes the computational system to acquire the second k-space data from a region of interest containing the breast tissue by controlling the magnetic resonance imaging system with the second pulse sequence commands. The first and second pulse sequence commands may be configured such that the region of interest for both acquisitions is from the same volume of space. Execution of the machine-executable instructions further causes the computational system to reconstruct the echo planar diffusion-weighted magnetic resonance image from the first k-space data. Execution of the machine-executable instructions further causes the computational system to reconstruct the fat-suppressed T2-weighted magnetic resonance image from the second k-space data.

In another embodiment the first pulse sequence commands are configured to acquire the first k-space data with a b-value between 0 s/mm$^2$ and 3000 s/mm$^2$.

In another embodiment the first pulse sequence commands are configured to acquire the first k-space data with a b-value between 800 s/mm$^2$ and 1600 s/mm$^2$. In some examples for this range the b-value may be considered to be a high b-value. This embodiment may be beneficial because the DWI detection of tissue types such as tumors work well when these b-values are used, but there are significant geometric distortions.

In another embodiment the first pulse sequence commands are configured to acquire the first k-space data with a b-value between 1200 s/mm$^2$ and 1400 s/mm$^2$. In some examples for this range the b-value may be considered to be a high b-value. This embodiment may be beneficial because the DWI detection of tissue types such as tumors works very effectively when these b-values are used, but there are significant geometric distortions.

In another embodiment the second pulse sequence commands are according to an electrical properties tomography magnetic resonance imaging protocol. An electrical properties tomography magnetic resonance imaging protocol may for example be a magnetic resonance imaging protocol that is used to measure distortions of the B1 magnetic field.

A number of fat-suppression pulses are compatible with electrical properties tomography. There are a variety of approaches but there are several main approaches which are mentioned. First, there may be a fat-suppression using an RF pulse that saturates fat protons selectively via the frequency of the fat-suppression RF pulse. Another approach is to use a Dixon-type technique which is similar to a chemical shift imaging. There are two images with different echo times that are acquired and processed to get a fat only and a water only image. The water only image in this example could be used for the fat-suppressed T2-weighted magnetic resonance image. Another approach is an inversion recovery method that utilizes that fat has a typically shorter T1 value than water does. All three of the above-mentioned methods used with a spin echo pulse sequence yields a phase measurement which may be used for EPT calculations.

In another embodiment the second pulse sequence commands are spin echo pulse sequence commands.

In another embodiment the second pulse sequence commands are ultrashort echo time pulse sequence commands.

In another embodiment the second pulse sequence commands are zero echo time pulse sequence commands.

In another embodiment the second pulse sequence commands are multi-echo gradient echo pulse sequence commands.

In another embodiment the second pulse sequence commands are balanced gradient echo pulse sequence commands.

In another embodiment the second pulse sequence commands are steady state precession pulse sequence commands. All the of the above-mentioned types of pulse sequence commands are compatible with measuring a phase which may be used for electrical properties tomography as well as performing a fat-suppression as was mentioned above.

In another embodiment execution of the machine-executable instructions further causes the computational system to reconstruct a conductivity map descriptive of the region of interest from the second k-space data. This embodiment may be beneficial because the spatially dependent conductivity is often dependent upon various ion concentrations. This in conjunction with identifying a region as being a high diffusion rate region or a region that has a diffusion rate above a predetermined criterion may be useful in classifying the tissue. For example, the classification could be used to rank the order in which the advisory regions should be investigated or suggested to investigate by the primary care physician or other healthcare professional.

In another embodiment the high diffusion rate regions are identified by thresholding the echo planar diffusion-weighted magnetic resonance image. In this example the high diffusion rate regions are defined by providing a threshold or predetermined diffusion rate which defines that region as having a high diffusion rate.

In another embodiment the image processing module is configured to algorithmically identify the advisory regions. In one example it is algorithmically identified by identifying one of the two tissue regions as one of the advisory regions if the one of the tissue regions has an overlap of any of the high diffusion rate regions above a predetermined overlap.

In another example the image processing module identifies one of the tissue regions as one of the advisory regions if the one of the tissue regions has a center distance with any of the other high diffusion rate regions below a predetermined distance. There may not be any overlap but if the centers are close enough, they may be classified as being the same region. The centers could for example be centroids. In another example the image processing module identifies one of the tissue regions as one of the advisory regions if the one of the tissue regions has a volume matching any of the high diffusion rate regions within a predetermined volume difference. The echo planar diffusion-weighted magnetic resonance image may cause a distortion of the shape and location of the high diffusion rate regions. Comparing the volumes may be one way of assigning the high diffusion rate regions to the proper tissue region.

The image processing module in another example may identify one of the tissue regions as one of the advisory regions if one of the tissue regions has a shape matching any of the high diffusion rate regions within a predetermined distortion.

In another embodiment the image processing module is a trained neural network that is configured to label a portion of the tissue regions as advisory regions in response to inputting the tissue regions and the high diffusion rate regions. The neural network may for example be trained by first having a number of tissue regions and high diffusion rate regions that are classified by a human. This may be used to make a training data. For example, then the neural network can be trained using a deep learning algorithm.

In another embodiment the tissue regions are non-fat tissue regions or non-adipose tissue regions.

In another aspect the invention provides for a computer program comprising machine-executable instructions for execution by a computational system controlling a medical system. For example, the computer program may be a computer program product stored on a non-transitory storage medium. Execution of the machine-executable instructions causes the computational system to receive an echo planar diffusion-weighted magnetic resonance image of a region of interest descriptive of breast tissue. Execution of the machine-executable instructions further causes the computational system to receive a fat-suppressed T2-weighted magnetic resonance image descriptive of the region of interest.

Execution of the machine-executable instructions further causes the computational system to segment the echo planar diffusion-weighted magnetic resonance image to identify high diffusion rate regions. Execution of the machine-executable instructions further causes the computational system to segment the fat-suppressed T2-weighted magnetic resonance image to identify tissue regions. Execution of the machine-executable instructions further causes the computational system to identify a portion of the tissue regions as advisory regions by inputting the high diffusion rate regions and the tissue regions into an image processing module. Execution of the machine-executable instructions further causes the computational system to provide the advisory regions as a segmentation of the fat-suppressed T2-weighted magnetic resonance image. The fat-suppressed T2-weighted magnetic resonance image may for example be displayed with the segmentation as an overlay.

In another aspect the method provides for a method of medical or magnetic resonance imaging. The method comprises receiving an echo planar diffusion-weighted magnetic resonance image of a region of interest descriptive of breast tissue. The method further comprises receiving a fat-suppressed T2-weighted magnetic resonance image descriptive of the region of interest. The method further comprises segmenting the echo planar diffusion-weighted magnetic resonance image to identify high diffusion rate regions. The method further comprises segmenting the fat-suppressed T2-weighted magnetic resonance image to identify tissue regions. The method further comprises identifying a portion of the tissue regions as an advisory region by inputting the high diffusion rate regions and tissue regions into an image processing module. The method further comprises providing the advisory regions as a segmentation of the fat-suppressed T2-weighted magnetic resonance image.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan. Magnetic resonance data is an example of tomographic medical image data.

A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
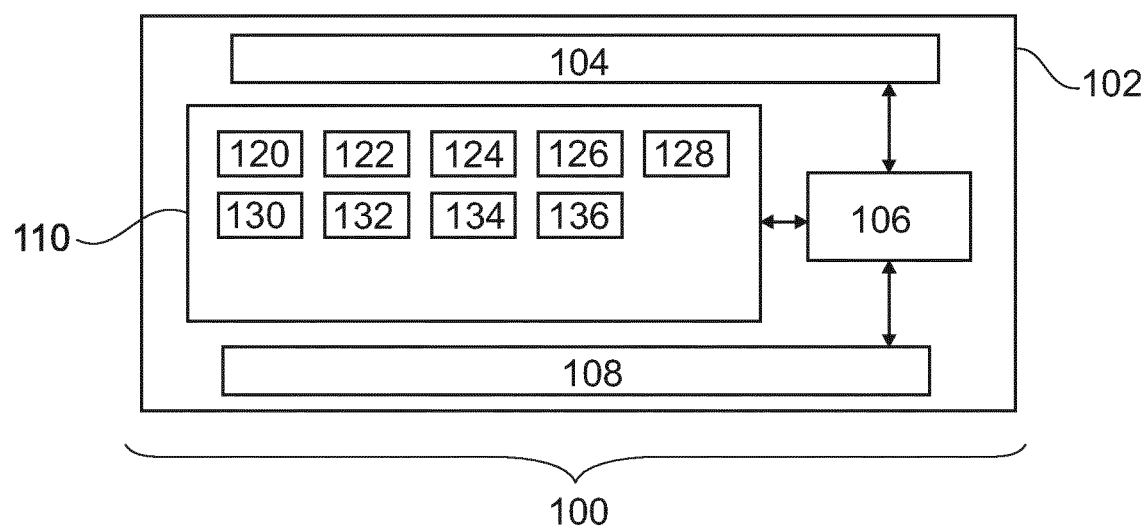
FIG. 1 illustrates an example of a medical system.

FIG. 1 illustrates an example of a medical system 100. In this example the medical system 100 comprises a computer with a computational system 106. The computer 102 may represent one or more computer systems that are networked together. The computational system 106 may for example represent one or more processors, microcontrollers or field programmable gate arrays. The computational system 106 is shown as being connected to an optional hardware interface 104, an optional user interface 108 and a memory 110. The hardware interface 104 may for example be used by the computational system 106 to control other components of the medical system 100 if they are present. User interface 108 may for example provide a means for an operator to control the medical system 100 as well as to display magnetic resonance images or other data. The memory 110 represents any type of memory which may be accessible to the computational system 106. The contents of the memory 110 may for example be divided between multiple storage or memory devices.

The memory 110 is shown as containing machine-executable instructions 120. The machine-executable instructions 120 contain instructions which enable the computational system 106 to control the operation and function of the medical system 100 as well as control any other additional components. The machine-executable instructions 120 may also enable the computational system 106 to perform various mathematical operations, data processing tasks, and image processing tasks. The memory 110 is further shown as containing echo planar diffusion-weighted magnetic resonance image 122. The memory 110 is further shown as containing fat-suppressed T2-weighted magnetic resonance image 124.

The memory 110 is shown as containing an optional registration 126 between the echo planar diffusion-weighted magnetic resonance image 122 and the fat-suppressed T2-weighted magnetic resonance image 124. In some instances, the two magnetic resonance images 122 and 124 may be acquired such that there is a one-to-one relation between their voxels. In other instances, the subject may have possibly moved and the registration 126 may contain a map so that the data between the two can be used. It is also noted that the echo planar diffusion-weighted magnetic resonance image 122 may have distortions in it, in which case slight deviations from a registration may not adversely affect operation of the medical system 100. This may also make a registration unnecessary.

The memory 110 is further shown as containing a number of high diffusion rate regions 128 that have been identified in the echo planar diffusion-weighted magnetic resonance image 122. This for example may be performed by thresholding the diffusion rate according to a predetermined threshold value for the diffusion. The memory 110 is further shown as containing tissue regions 130 that were identified in the fat-suppressed T2-weighted magnetic resonance image 124. The tissue regions 130 may for example be non-fat or non-adipose tissue regions that identify the location of tissue of the subject. The memory 110 is further shown as containing an image processing module 132. The image processing module 132 outputs a number of advisory regions 134 that are selected from the tissue regions 130. They are selected by correlating or matching the high diffusion rate regions 128 to the tissue regions 130. The memory 110 is further shown as containing an optional augmented T2-weighted magnetic resonance image 136 which shows the advisory regions 134 overlaid or emphasized on the fat-suppressed T2-weighted magnetic resonance image 124.

Figure 2:
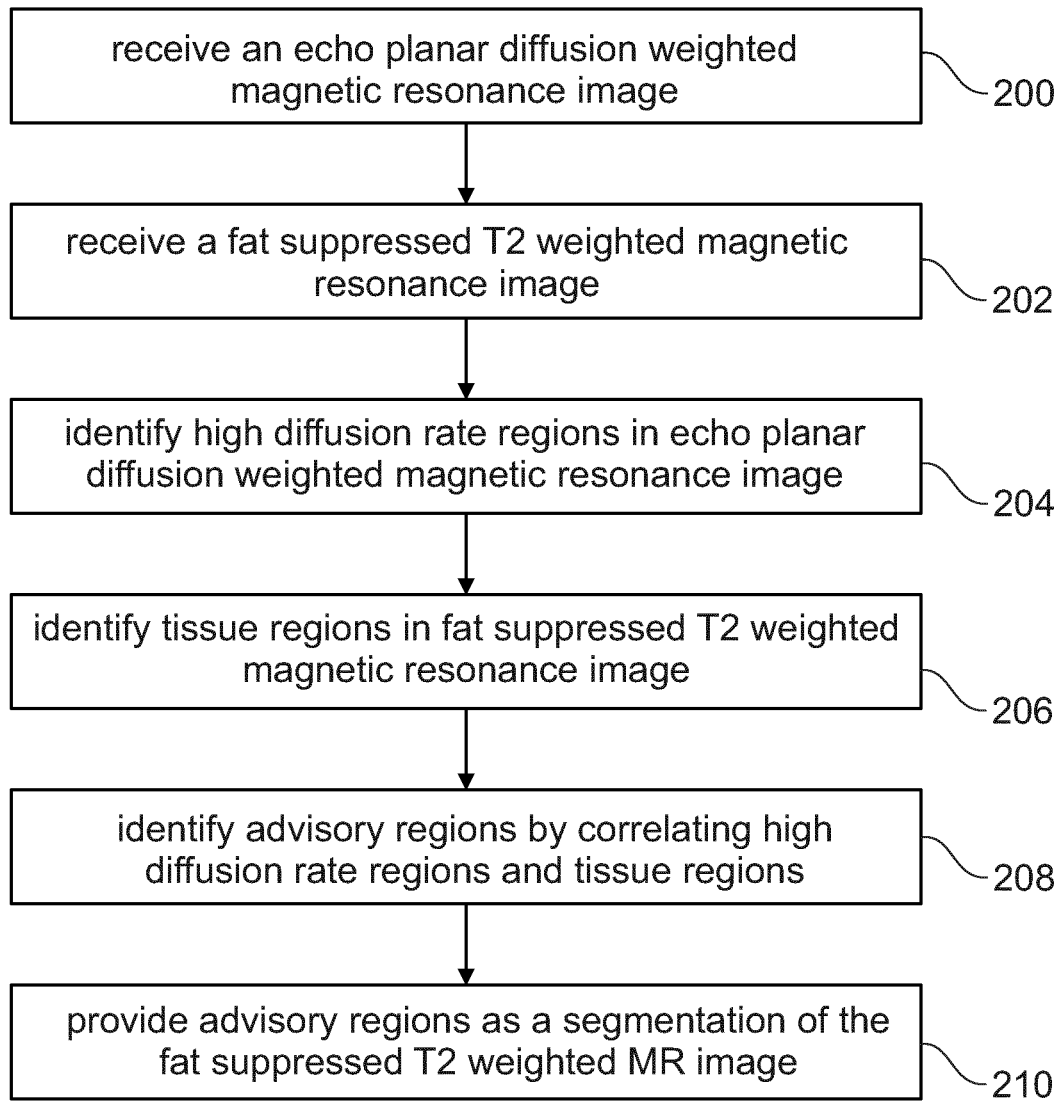
FIG. 2 shows a flow chart which illustrates a method of operating the medical system of FIG. 1.

FIG. 2 shows a flowchart which illustrates a method of operating the medical system 100 of FIG. 1. First in step 200 the echo planar diffusion-weighted magnetic resonance image 122 is received. Next in step 202 the fat-suppressed T2-weighted magnetic resonance image 124 is received. Then, in step 204, the echo planar diffusion-weighted magnetic resonance image 122 is segmented to identify the high diffusion rate regions 128. Next, in step 206, the fat-suppressed T2-weighted magnetic resonance image 124 is segmented to identify the tissue regions 130. In step 208 the high diffusion rate regions 128 and the tissue regions 130 are input into the image processing module 132 to provide or identify a portion of the tissue regions 130 as the advisory regions 134. Finally, in step 210, the advisory regions 134 are provided as a segmentation of the fat-suppressed T2-weighted magnetic resonance image.

Figure 3:
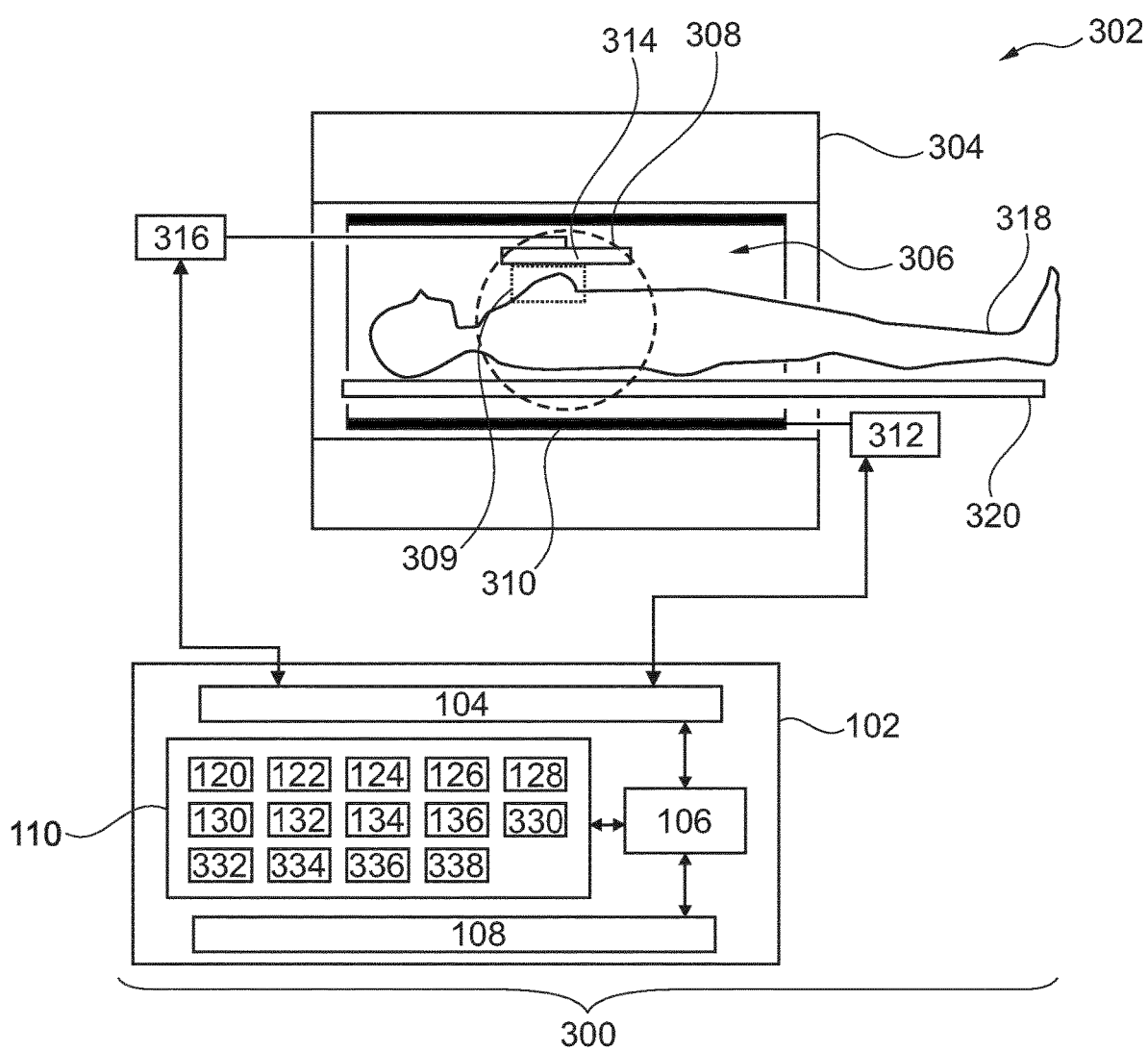
FIG. 3 illustrates a further example of a medical system.

FIG. 3 illustrates a further example of a medical system 300. The medical system 300 in FIG. 3 is similar to the medical system 100 in FIG. 1 except that it additionally comprises a magnetic resonance imaging system 302 that can be controlled by the computational system 106.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. A region of interest 309 is shown within the imaging zone 308. The magnetic resonance data is acquired from the region of interest. A subject 318 is shown as being supported by a subject support 320 such that at least a portion of the subject 318 is within the imaging zone 308 and the region of interest 309. Within the region of interest 309 it can be seen that there is breast tissue of the subject 318.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 are connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receiver. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The transceiver 316 and the gradient controller 312 are shown as being connected to the hardware interface 106 of a computer system 102.

The memory 110 is further shown as containing first pulse sequence commands 330 that are configured to acquire first k-space data according to an echo planar diffusion-weighted magnetic resonance imaging protocol. The memory 110 is further shown as containing the first k-space data 332 that was acquired by controlling the magnetic resonance imaging system 302 with the first pulse sequence commands 330. The echo planar diffusion-weighted magnetic resonance image 122 is reconstructed from the first k-space data 332. The memory 110 is further shown as containing second pulse sequence commands 334. The second pulse sequence commands 334 are configured to acquire second k-space data according to a T2-weighted magnetic resonance imaging protocol.

In the example illustrated in FIG. 3 second pulse sequence commands 334 are configured for acquiring a phase measurement which is suitable for electrical properties tomography. The memory 110 is shown as containing second k-space data 336 that was acquired by controlling the magnetic resonance imaging system 302 with the second pulse sequence commands 334. The second k-space data 336 was used to reconstruct the fat-suppressed T2-weighted magnetic resonance image 124 and also a conductivity map 338. The conductivity map 338 is shown as being stored in the memory 110.

Magnetic Resonance (MR) methods for breast cancer investigations are usually based on administration of contrast agent (e.g., for dynamic contrast enhanced (DCE) imaging), which is regarded as a major drawback for general MR-based breast cancer screening.

"Electrical Properties Tomography" (EPT) may have in general the same potential for breast lesion characterization as DCE. However, the determination of conductivity in the state of the art needs the support of contrast agent for reliable tumor boundary detection, and thus, a contrast-agent free version of breast cancer EPT is still missing.

Examples may (a) to perform a first, highly sensitivity MR sequence A 330 (e.g. high b-value EPI-DWI) showing only tumor tissue but geometrically distorted (the echo planar diffusion weighted magnetic resonance image 122), (b) to perform a second, EPT-suitable MR sequence B 334 (e.g., fat-suppressed T2-weighted imaging) showing many potential lesions but without geometrical distortions (the fat suppressed T2 weighted magnetic resonance image), (c) identifying the correct tumor lesion of sequence B by searching for the maximum geometric overlap between distorted lesion of sequence A and potential lesions of sequence B (identify the advisory regions 134), and optionally (d) characterizing type of this tissue by its conductivity reconstructed from sequence B.

The main potential of EPT is not the identification (localization) of a tumor, but the possible characterization of a suspicious advisory region or tumor. Identification/localization of a tumor is usually performed by DCE. Examples suggests to replace DCE by a first sequence (sequence A). Sequence A is similarly sensitive as DCE, as given for instance by EPI-based diffusion weighted imaging (DWI) with high b-value. In a second step, potential lesions as identified by EPI-DWI are characterized by EPT. Since EPT cannot be performed by post-processing EPI-DWI, a second, dedicated EPT scan (sequence B, e.g. fat-suppressed T2-weighted (T2w) imaging) is required. To enable EPT, sequence B has a phase which is (i) purely B1-related and (ii) has a sufficient intrinsic contrast between tumor versus fat and tumor versus glandular tissue.

(i) A purely B1-related phase can be given by spin-echo based sequences, sequences with balanced gradients (steady-state-free-precession), or ultrashort/zero-TE sequences. Multi-echo gradient echo sequences allow in principle the voxel-by-voxel extrapolation of phase evolution to TE=0 equivalent to the B1-related phase, however, requiring a potentially unstable and thus error-prone extrapolation algorithm.

(ii) Sufficient intrinsic contrast between tumor versus fat and tumor versus glandular tissue may be beneficial, since numerical differentiation of phase requires the usage of an ensemble of neighbor voxels around the target voxel (the so-called "kernel"), which preferably contain only voxels with similar conductivity. Thus, a-priori knowledge about tumor boundaries is required to shape the kernel locally to stay inside the tumor volume. These tumor boundaries could be taken from a different scan. However, taking tumor boundaries and phase from separate scans is always problematic due to the risk of imperfect image registration. Particularly for small tumors, erroneously including only a few mis-registered non-tumor voxels can significantly tamper conductivity results.

Figure 4:
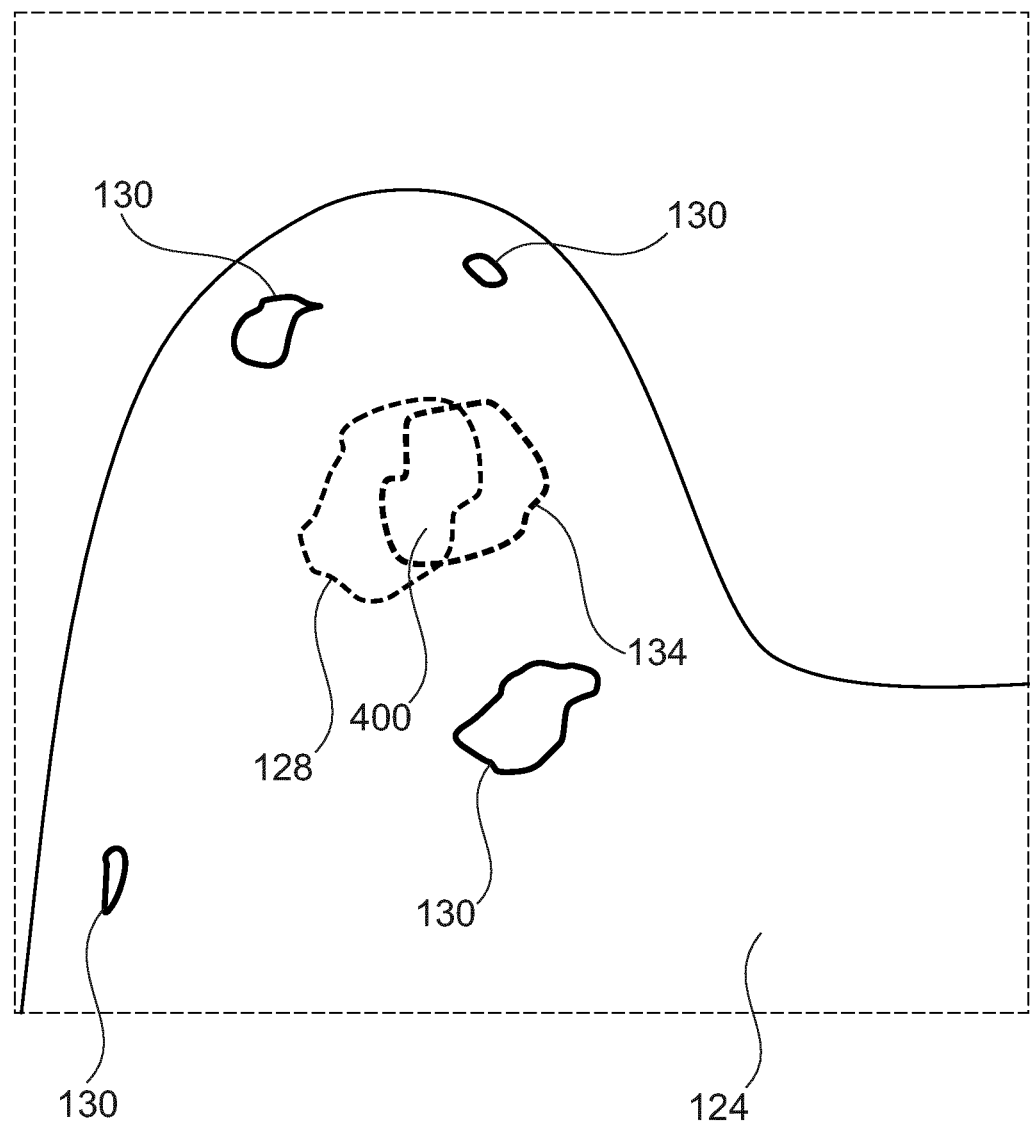
FIG. 4 illustrate a method of selecting an advisory region.

FIG. 4 illustrates one means of identifying an advisory region 134. FIG. 4 shows a sketch which represents a fat-suppressed T2-weighted magnetic resonance image 124. The regions labeled 130 and also 134 represent tissue regions 130. The region 128 represents a high diffusion rate region that was identified in an echo planar diffusion-weighted magnetic resonance image 122. The echo planar diffusion-weighted magnetic resonance image 122 contains distortions and it is unable to positively identify the location of the advisory region 134. Examining this it can be seen that there is an overlap region 400 between the curves 128 and 134. Region 134 is then identified as an advisory region. From comparing the two it is clear that the region 134 is the region which has the high diffusion rate and should therefore be further investigated by a physician.

The region of the overlap 400 can be compared to the area of the curve 134. If this is above a certain fraction then this may be a predetermined overlap which can be used to trigger the identification of the advisory region 134. Likewise, a center or centroid of the region 128 and 134 could also be identified and a distance between them could be compared. Also examining FIG. 4 it can be seen that the volume of the region 128 and the volume of the region 134 are the most similar. This may also be an alternative means of identifying the advisory region 134. It can also be seen that the shape of the region 128 and the shape of the region 134 are the most similar when compared with the other tissue regions 130. The shape or deformation needed to match region 128 to 134 may also therefore be used to identify the advisory region 134.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 computer
104 hardware interface
106 computational system
108 user interface
110 memory
120 machine executable instructions
122 echo planar diffusion weighted magnetic resonance image
124 fat suppressed T2 weighted magnetic resonance image
126 optional registration
128 high diffusion rate regions
130 tissue regions
132 image processing module
134 advisory regions
136 augmented T2 weighted magnetic resonance image
200 receive an echo planar diffusion weighted magnetic resonance image of a region of interest descriptive of breast tissue
202 receive a fat suppressed T2 weighted magnetic resonance image descriptive of the region of interest
204 segment the echo planar diffusion weighted magnetic resonance image to identify high diffusion rate regions
206 segment the fat suppressed T2 weighted magnetic resonance image to identify tissue regions
208 identify a portion of the tissue regions as advisory regions by inputting the high diffusion rate regions and the tissue regions into an image processing module
210 provide the advisory regions as a segmentation of the fat suppressed T2 weighted magnetic resonance image
300 medical system
302 magnetic resonance imaging system
304 magnet
306 bore of magnet
308 imaging zone
309 region of interest
310 magnetic field gradient coils
312 magnetic field gradient coils power supply
314 radio-frequency coil
316 transceiver
318 subject
320 subject support
330 first pulse sequence commands
332 first k-space data
334 second pulse sequence commands
336 second k-space data
338 conductivity map
400 overlapping region

The invention claimed is:

1. A medical system comprising:
a non-transitory memory configured to store machine executable instructions;
a computational system configured to control the medical system, wherein execution of the machine executable instructions causes the computational system to:
receive an echo planar diffusion weighted magnetic resonance image of a region of interest descriptive of breast tissue;
receive a fat suppressed T2 weighted magnetic resonance image descriptive of the region of interest;
segment the echo planar diffusion weighted magnetic resonance image to identify high diffusion rate regions wherein the high diffusion rate regions are regions with a diffusion rate above a predetermined diffusion rate threshold;
segment the fat suppressed T2 weighted magnetic resonance image to identify tissue regions;
process the high diffusion rate regions and the tissue regions to identify a portion of the tissue regions as advisory regions;
receive a conductivity map descriptive of the region of interest;
calculate a conductivity measure of each of the advisory regions using the conductivity map;
assign a classification of each of the advisory regions according to the conductivity measure; and
provide the advisory regions as a segmentation of the fat suppressed T2 weighted magnetic resonance image.

2. The medical system of claim 1, wherein the echo planar diffusion weighted magnetic resonance image is a high b-value echo planar diffusion weighted magnetic resonance image, wherein the high b-value is a b-value at or above 800 s/mm$^2$.

3. The medical system of claim 1, wherein the medical system further comprises a magnetic resonance imaging system configured to acquire k-space data from an imaging zone, wherein the memory further contains first pulse sequence commands and second pulse sequence commands, wherein the first pulse sequence commands are configured to acquire first k-space data according to an echo planar diffusion weighted magnetic resonance imaging protocol, wherein the second pulse sequence commands are configured to acquire second k-space data according to a T2-weighted magnetic resonance imaging protocol, wherein the second pulse sequence commands are according to an electrical properties tomography magnetic resonance imaging protocol, wherein the second pulse sequence commands are fat suppressing, wherein execution of the machine executable instructions further causes the computational system to:
acquire the first k-space data from the region of interest containing the breast tissue by controlling the magnetic resonance imaging system with the first pulse sequence commands;
acquire the second k-space data from the region of interest containing the breast tissue by controlling the magnetic resonance imaging system with the second pulse sequence commands;
reconstruct the echo planar diffusion weighted magnetic resonance image from the first k-space data;
reconstruct the fat suppressed T2 weighted magnetic resonance image from the second k-space data; and
reconstruct a conductivity map descriptive of the region of interest from the second k-space data.

4. The medical system of claim 3, wherein the first pulse sequence commands are configured to acquire the first k-space data with a b-value between 0 s/mm$^2$ and 3000 s/mm$^2$.

5. The medical system of claim 3, wherein the second pulse sequence commands are any one of the following:
   spin echo pulse sequence commands;
   ultrashort echo time pulse sequence commands;
   zero echo time pulse sequence commands;
   multi-echo gradient echo pulse sequence commands;
   balanced gradient echo pulse sequence commands; and
   steady state free precession pulse sequence commands.

6. The medical system of claim 3, wherein the advisory regions are used to define boundaries during calculation of the conductivity map.

7. The medical system of claim 3, wherein the first pulse sequence commands are configured to acquire the first k-space data with a b-value between 800 s/mm$^2$ and 1600 s/mm$^2$.

8. The medical system of claim 3, wherein the first pulse sequence commands are configured to acquire the first k-space data with a b-value between 1200 s/mm$^2$ and 1400 s/mm$^2$.

9. The medical system of claim 1, wherein execution of the machine-executable instructions further causes the computational system to render the advisory regions as an overlay on the fat-suppressed T2-weighted magnetic resonance image.

10. The medical system of claim 9, wherein execution of the machine executable instructions further causes the computational system to rank renderings of the advisory regions using the conductivity measure.

11. The medical system of claim 1, wherein the high diffusion rate regions are identified by thresholding the echo planar diffusion weighted magnetic resonance image.

12. The medical system of claim 1, wherein the processing is configured to algorithmically identify the advisory regions by performing at least one of the following:
   identify one of the tissue regions as one of the advisory regions if the one of the tissue regions has an overlap with any of high diffusion rate regions above a predetermined overlap;
   identify one of the tissue regions as one of the advisory regions if the one of the tissue regions has a center distance with any of high diffusion rate regions below a predetermined distance;
   identify one of the tissue regions as one of the advisory regions if the one of the tissue regions has a volume matching any of high diffusion rate regions within a predetermined volume difference; or
   identify one of the tissue regions as one of the advisory regions if the one of the tissue regions has a shape matching any of high diffusion rate regions within a predetermined distortion.

13. The medical system of claim 1, wherein a trained neural network is configured to label the portion of the tissue regions as advisory regions in response to processing the tissue regions and the high diffusion rate regions.

14. The medical system of claim 1, wherein the tissue regions are non-fat tissue regions.

15. A computer program stored on a non-transitory computer readable medium comprising machine executable instructions for execution by a computational system, wherein execution of the machine executable instructions causes the computational system to:
   receive an echo planar diffusion weighted magnetic resonance image of a region of interest descriptive of breast tissue;
   receive a fat suppressed T2 weighted magnetic resonance image descriptive of the region of interest;
   segment the echo planar diffusion weighted magnetic resonance image to identify high diffusion rate regions, wherein the high diffusion rate regions are regions with a diffusion rate above a predetermined diffusion rate threshold;
   segment the fat suppressed T2 weighted magnetic resonance image to identify tissue regions;
   process the high diffusion rate regions and the tissue regions to identify a portion of the tissue regions as advisory regions; and
   receive a conductivity map descriptive of the region of interest;
   calculate a conductivity measure of each of the advisory regions using the conductivity map;
   assign a classification of each of the advisory regions according to the conductivity measure; and
   provide the advisory regions as a segmentation of the fat suppressed T2 weighted magnetic resonance image.

16. A method of medical imaging, wherein the method comprises;
   receiving an echo planar diffusion weighted magnetic resonance image of a region of interest descriptive of breast tissue;
   receiving a fat suppressed T2 weighted magnetic resonance image descriptive of the region of interest;
   segmenting the echo planar diffusion weighted magnetic resonance image to identify high diffusion rate regions, wherein the high diffusion rate regions are regions with a diffusion rate above a predetermined diffusion rate threshold;
   segmenting the fat suppressed T2 weighted magnetic resonance image to identify tissue regions;
   processing the high diffusion rate regions and the tissue regions to identify a portion of the tissue regions as advisory regions;
   receiving a conductivity map descriptive of the region of interest;
   calculating a conductivity measure of each of the advisory regions using the conductivity map;
   assigning a classification of each of the advisory regions according to the conductivity measure; and
   providing the advisory regions as a segmentation of the fat suppressed T2 weighted magnetic resonance image.

* * * * *